United States Patent
Danielson et al.

(10) Patent No.: US 6,270,807 B1
(45) Date of Patent: Aug. 7, 2001

(54) TASTE-MASKED PHARMACEUTICAL COMPOSITION

(75) Inventors: Douglas Willard Danielson, Otsego; Shirish A. Shah, Kalamazoo, both of MI (US)

(73) Assignee: L. Perrigo Company, Allegan, MI (US)

( * ) Notice: Subject to any disclaimer, the term of this patent is extended or adjusted under 35 U.S.C. 154(b) by 0 days.

(21) Appl. No.: 09/261,287

(22) Filed: Mar. 2, 1999

(51) Int. Cl.⁷ .............................. A61K 9/20; A61K 9/50
(52) U.S. Cl. ........................ 424/497; 424/441; 424/465; 424/490; 514/772.3; 514/777; 514/781; 514/951; 514/974
(58) Field of Search .................................... 424/441, 464, 424/465, 497, 490, 482, 493; 514/974

(56) References Cited

U.S. PATENT DOCUMENTS

| | | |
|---|---|---|
| 4,283,408 | 8/1981 | Hirata et al. . |
| 4,800,087 | 1/1989 | Mehta . |
| 4,961,890 | 10/1990 | Boyer . |
| 4,971,791 | 11/1990 | Tsau et al. . |
| 4,975,281 | 12/1990 | Harwood et al. . |
| 5,073,374 | 12/1991 | McCarty . |
| 5,075,114 | 12/1991 | Roche . |
| 5,084,278 | 1/1992 | Mehta . |
| 5,215,755 | 6/1993 | Roche et al. . |
| 5,229,134 | 7/1993 | Mention et al. . |
| 5,229,137 | 7/1993 | Wolfe . |
| 5,260,072 | 11/1993 | Roche et al. . |
| 5,275,823 | 1/1994 | France et al. . |
| 5,286,489 | 2/1994 | Tsau et al. . |
| 5,286,493 | 2/1994 | Oshlack et al. . |
| 5,320,855 | 6/1994 | Roche et al. . |
| 5,425,950 | 6/1995 | Dandiker et al. . |
| 5,431,916 | 7/1995 | White . |
| 5,460,825 | 10/1995 | Roche et al. . |
| 5,464,632 * | 11/1995 | Cousin et al. ........................ 424/465 |
| 5,489,436 | 2/1996 | Hoy et al. . |
| 5,529,783 | 6/1996 | Burke et al. . |
| 5,552,152 | 9/1996 | Shen . |
| 5,578,316 | 11/1996 | Bhardwaj et al. . |
| 5,593,685 | 1/1997 | Bye et al. . |
| 5,593,696 | 1/1997 | McNally et al. . |
| 5,622,980 | 4/1997 | Caldwell et al. . |
| 5,629,026 | 5/1997 | Davis . |
| 5,656,652 | 8/1997 | Davis . |
| 5,679,376 | 10/1997 | Stevens et al. . |
| 5,695,784 * | 12/1997 | Pollinger et al. ..................... 424/495 |
| 5,705,189 | 1/1998 | Lehmann et al. . |
| 5,725,880 | 3/1998 | Hirakawa et al. . |
| 5,760,094 | 6/1998 | Alexander et al. . |
| 5,773,031 | 6/1998 | Shah et al. . |
| 5,814,336 | 9/1998 | Kelm et al. . |
| 5,817,340 | 10/1998 | Roche et al. . |

* cited by examiner

*Primary Examiner*—James M. Spear
(74) *Attorney, Agent, or Firm*—Price, Heneveld, Cooper, DeWitt & Litton

(57) ABSTRACT

A chewable dosage form containing a histamine $H_2$-receptor antagonist in an amount which is effective to treat a gastrointestinal disorder is provided in a palatably acceptable form. The dosage form comprises granules containing the histamine $H_2$-receptor antagonist, which are provided with a taste-masking coating comprising a water-insoluble, water-permeable methacrylate ester copolymer in which the coating is applied to the granules in an amount which provides a taste-masking effect for a relatively short period during which the composition is being chewed by a patient, but which allows substantially immediate release of the histamine $H_2$-receptor antagonist after the composition has been chewed and ingested.

20 Claims, No Drawings

TASTE-MASKED PHARMACEUTICAL COMPOSITION

FIELD OF THE INVENTION

This invention relates to pharmaceutical compositions for treating gastrointestinal distress, episodic heartburn, and the like, and more particularly to taste-masked, chewable pharmaceutical compositions containing a histamine $H_2$-receptor antagonist.

BACKGROUND OF THE INVENTION

It is known that certain histamine $H_2$-receptor antagonists are routinely administered orally to patients suffering from certain gastrointestinal conditions such as ulcers, dyspepsia, various reflux indications, and the like. Examples of commonly used histamine $H_2$-receptor antagonist include cimetidine, ranitidine and famotidine. These compounds are usually administered orally in the form of tablets or capsules which are intended to be swallowed. Thus, for a substantial portion of patients being treated with a histamine $H_2$-receptor antagonist, the taste of the histamine $H_2$-receptor antagonist is unimportant. However, there are many segments of the patient population which have difficulty swallowing tablets, and would prefer a more easily ingested dosage form, such as a chewable tablet. Unfortunately, the histamine $H_2$-receptor antagonists are known to have an unpalatably bitter taste which must be effectively masked to ensure good patient compliance with chewable tablets.

Attempts to produce palatably acceptable chewable pharmaceutical compositions comprising a histamine $H_2$-receptor antagonist include efforts to mask the bitter taste of the histamine $H_2$-receptor antagonist with a drug adsorbate, such as a synthetic cationic resin or a silicate taste-masking agent. Other attempts involve the use of an intense sweetener such as aspartame, or the like. Still other attempts have involved the use of a polymeric coating. For example, U.S. Pat. No. 5,260,072 to Roche et al. proposes a chewable tablet of a histamine $H_2$-receptor antagonist comprising granules which are formed by rotogranulation of the medicament with a binder and a fine particulate carrier material, and are coated with a polymer blend of cellulose acetate, cellulose acetate butyrate or a combination of both along with polyvinylpyrrolidone.

These attempts at providing a palatably acceptable chewable pharmaceutical composition have not been entirely successful. Accordingly, there remains a need for effective methods of taste-masking histamine $H_2$-receptor antagonists for the preparation of palatably acceptable chewable tablets.

SUMMARY OF THE INVENTION

The present invention provides a chewable pharmaceutical composition comprising a granulated histamine $H_2$-receptor antagonist in which the individual granules are provided with a taste-masking coating comprising a water-insoluble, water-permeable methacrylate ester copolymer. The coating is applied to the granules in an amount which provides a taste-masking effect for a relatively short period during which the composition is being chewed by a patient, but which allows substantially immediate release of the histamine $H_2$-receptor antagonist after the composition has been chewed and ingested.

DESCRIPTION OF THE PREFERRED EMBODIMENTS

Histamine $H_2$-receptor antagonist are derivatives of histamine that bind to and exhibit inhibiting or blocking activity against $H_2$-receptors. The histamine $H_2$-receptor antagonists, or $H_2$-blocking agents, are a discrete and limited group of medications readily recognized in the art, and are generally polar, hydrophilic molecules. Most pharmaceutical formulations which employ histamine $H_2$-receptor antagonist, however, have an unpalatably bitter taste. Examples of histamine $H_2$-receptor antagonist include, but are not limited to, ranitidine, cimetidine, nizatidine, famotidine, sufotidine, roxatidine, bisfentidine, tiotidine, lamtidine, niperotidine, mifentidine, zaltidine and loxtidine. Preferred histamine $H_2$-receptor antagonist include cimetidine, ranitidine, and especially famotidine.

The pharmaceutically active agents useful in the present invention are preferably provided in the form or a pharmaceutically acceptable salt or a free base. Suitable salts are readily available and well known in the art. The preferred pharmaceutically acceptable salts are water-soluble. The histamine $H_2$-receptor antagonist may be provided in a variety of water-soluble salt forms. Suitable water-soluble salt forms include hydrochloride salts, hydrobromide salts, sulfate salts, nitrate salts, citrate salts and tartrate salts.

The amount of histamine $H_2$-receptor antagonist, either in salt form or free base, which is included in the composition of the present invention will be dependent upon the pharmaceutical activity of the particular compound. Generally, the amount of histamine $H_2$-receptor antagonist is sufficient to deliver a therapeutically effective dose to a patient in need thereof. For example, the amount of histamine $H_2$-receptor antagonist typically included in the composition is between about 1 to about 50% by weight. Preferably, the amount of histamine $H_2$-receptor antagonist included in the composition is sufficient to provide an oral dosage form containing between about 2 to about 20% by weight of histamine $H_2$-receptor antagonist.

The granules containing the histamine $H_2$-receptor antagonist are preferably formed by blending the histamine $H_2$-receptor antagonist, a pharmaceutically acceptable binder such as povidone (polyvinylpyrrolidone), and a carrier which adds bulk and smoothness to the body of the granules. Pharmaceutically acceptable binders, carriers, diluents, disintegrants, etc. are described in the "Handbook of Pharmaceutical Excipients," 2nd Ed., 1994, which is incorporated here by reference.

Povidone or polyvinylpyrrolidone acts as a binder in the granulation process. Use of povidone as a binder imparts good mechanical strength to the granules. In this respect, povidone is superior to other binders such as cellulosic polymers, but other polymers may be used, e.g., hydroxypropyl methylcellulose or starch.

Lactose is a carrier which adds bulk and smoothness to the body of the granules and may increase the release rate and dissolution of the histamine $H_2$-receptor antagonist, after the composition has been chewed and swallowed. Other useful carrier materials which may be substituted for lactose include other saccharides, e.g., fructose, sucrose, dextrose, confectioner's sugar and maltodextrins. The carrier material should be of a fine particle size, preferably in the range of 5 to 75 microns to fill in surface voids and provide a smooth surface to the granules.

Further, microcrystalline cellulose may be blended into the carrier materials and incorporated into the granules. Fine particle size microcrystalline cellulose may be added to such carrier materials in the range of about 5 to 20% of the weight of the granules, to provide increased strength to the granules.

The histamine $H_2$-receptor antagonist may comprise from about 2 to about 85% of the weight of the granules, with the binder comprising from about 1 to about 10% of the weight of the granules, and with the carrier comprising from about 10 to about 90% of the weight of the granules.

The exact size of the coated granules is not critical. However, the granules are preferably sized in the range of from about 150 to about 2000 microns. The preferred range is 300–1250 µm. In general, particles of like size facilitate blending and provide regularity in dosage forms. The granules may be prepared using well known wet granulating techniques.

The granules containing the histamine $H_2$-receptor antagonist are provided with a polymeric coating comprising a methacrylate ester copolymer. The polymeric coating is applied in an amount which is sufficient to mask the taste of the histamine $H_2$-receptor antagonist so that the resulting chewable tablets containing the coated granules have an acceptable palatability as they are chewed and swallowed. At the same time, the amount of coating is sufficiently low so that substantially immediate release of the histamine $H_2$-receptor antagonist is achieved after the pharmaceutical composition is chewed and swallowed, e.g., immediate release in the stomach.

The methacrylate ester copolymer is a water-insoluble, water-permeable, and slightly water-swellable polymer. The polymeric coating is not soluble in the gastrointestinal fluids and is not sensitive to the pH thereof, i.e., the water-permeability of the coating is not a function of pH, or is only very slightly dependent on pH. The polymeric coating preferably comprises a methacrylate ester copolymer having the general formula:

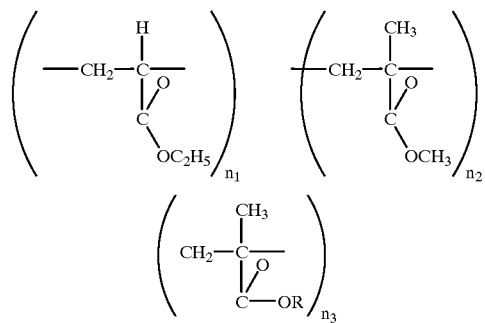

wherein R is an alkyl group having from 2 to 12 carbon atoms or an aminoalkyl group having from 1 to about 12 carbon atoms, and wherein $n_1$, $n_2$ and $n_3$ are selected so that the polymer has a molecular weight of from about 100,000 to about 1,000,000. The ratio $n_1$: $n_2$ is from about 1:2 to about 2:1, and the ratio of $n_3$:$(n_1+n_2)$ is from about 0 to about 1:15. Particularly preferred are copolymers of ethylacrylate and methylmethacrylate, although other copolymers such as terpolymers and other copolymers comprising three or more different monomeric units having properties similar to ethylacrylate-methylmethacrylate copolymers are also preferred. The preferred ethylacrylate-methylmethacrylate copolymer has a molecular weight of approximately 800,000. A particularly preferred ethylacrylate-methylmethacrylate copolymer is Eudragrit® NE30D which is commercially available from Röhm Pharmaceuticals.

The polymer coating can be applied to the particles containing an $H_2$-receptor antagonist in any suitable manner. Preferably, the polymeric film is applied as a uniform coating having a smooth surface structure and a relatively constant thickness. For example, the polymer coating may be applied to the granules by utilizing pneumatic spray guns.

The pneumatic spray guns may have a nozzle diameter of from about 0.8 millimeters to about 2 millimeters and may be operated at a coating solution atomization air pressure of from about 0.5 to about 3 bar. The spraying rate of the spray guns may be easily regulated using peristaltic pumps or pressure vessels. Ideally, spraying should be continuous with simultaneous drying so that the granules do not become too moist (overly wet). The freshly sprayed polymer coating should dry as quickly as possible to avoid agglomeration of the particles. Other suitable methods include the use of fluidized-bed processes. Modified coating drums (usually cylindrical horizontally rotating units with a perforated wall) are also suitable for coating the granules.

The polymer coating composition is preferably an aqueous solution containing a methacrylate ester copolymer of the type described above. The coating composition may include minor amounts of emulsifiers, wetting agents, drying agents, curing accelerators and stabilizers. For example, glyceryl monostearate may be added to the coating solution as a tackiness reducing agent which prevents granule growth through agglomeration. Minor amounts of talc can also be incorporated into the coating composition or subsequently applied to improve or enhance flow properties of the coated granules.

The thickness of the polymer coating can range from about 2 microns to about 20 microns, and the weight of the coating is generally from about 2 to about 20% of the weight of the coated granule. Because the coating is relatively thin, the coated granules are substantial in the same size range as the uncoated granules, i.e., from about 150 to about 2000 microns.

The polymer coated granules can be further manufactured into chewable tablets by compressing the polymer coated granules, either alone or in combination with extra-granular excipients, adjuvants, fillers, and/or other active ingredients. For example, fillers, lubricants, binders, compression aids, disintigrants, flavoring agents, sweeteners and wetting agents may be employed. The chewable tablets can also contain solid diluents, such as sugars and sugar alcohols such as lactose, xylitol, sorbitol and mannitol. Where desired, intense sweeteners can be added, for example ammonium glycyrrhizinate, sodium cyclamate, sodium saccharinate and aspartame. Useful binders include acacia, tragacanth, gelatin, sucrose, pre-gelatinized starch, starch, sodium alginate, methylcellulose, sodium carboxymethyl cellulose, ethyl cellulose, hydroxypropylmethyl cellulose, polyvinylpyrrolidone, and polyacrylamide. Examples of disintegrants include crosslinked polyvinylpyrrolidone, starch derivatives such as sodium carboxymethyl starch and cellulose derivatives. Lubricants, guildants and anti-adhesive agents include metallic stearates such as magnesium stearate, talc, and high melting point waxes. Typical compression aids include microcrystalline cellulose, dicalcium phosphate and compressible sugar. To further assist patient compliance, the tablets can also contain flavorants such as fruit flavors, mint flavors, and the like. Other ingredients which may be added and are described in the "*Handbook of Pharmaceutical Excipients*", 2nd Ed, 1994 and "*Food Chemicals Index*", 3rd Ed.

The polymer coated granules containing a histamine $H_2$-receptor antagonist may be thoroughly mixed with any desired excipients, adjuvants, fillers and the like, and directly compressed into chewable tablets employing the appropriate punches and dies.

The present invention is illustrated in more detail by the following example, which is intended to be illustrative, and should not be interpreted as limiting or otherwise restricting the scope of the invention.

EXAMPLE

Polymer coated granules containing famotidine are prepared by combining 16.7 kilograms of famotidine, 88 kilograms of lactose, and 8.33 kilograms of microcrystalline cellulose, dry blending the famotidine lactose and microcrystalline cellulose, and passing the dry blend through a Number 10 mesh screen. A granulating solution comprising 14.9 kilograms water, and 3.33 kilograms povidone is prepared by combining the water and povidone in a mixing tank and mixing for about 25 minutes. The powder blend comprising famotidine, lactose and microcrystalline cellulose is combined with the granulating solution to form granules in a conventional granulating apparatus.

A taste-masking polymer coating solution is prepared by combining 27.8 kilograms of Eudragit® NE30D (methacrylate ester copolymer), 0.33 kilograms glyceryl monostearate, and 13 kilograms water. A Glatt coater (top spray) is used to apply the coating solution to the granules. Talc may be added to accelerate curing and improve powder flow characteristics. The resulting coated granules are passed through a Number 60 mesh screen.

Thereafter, the coated granules are compounded with aspartame, maltodextrin, mannitol, microcrystalline cellulose, red iron oxide, sodium starch glycolate, peppermint, corn starch, and magnesium stearate. The resulting mixture is directly compressed into chewable tablets.

It will be apparent to those skilled in the art that various modifications to the preferred embodiment of the invention as described here and can be may without departing from the spirit or scope of the invention as defined by the appended claims, which are to be interpreted in accordance with the principles of Patent Law including the doctrine of equivalents.

The embodiments of the invention in which an exclusive property or privilege is claimed are defined as follows:

1. A chewable dosage form comprising:
    a histamine $H_2$-receptor antagonist in an amount which is effective to treat a gastrointestinal disorder, the histamine $H_2$-receptor antagonist selected from the group consisting of ranitidine, nizatidine, famotidine, sufotidine, roxatidine, bisfentidine, tiotidine, lamtidine, niperotidine, mifentidine, zaltidine and loxtidine, the histamine $H_2$-receptor antagonist being present in the form of granules which are provided with a polymeric coating, the polymeric coating being present in an amount which is sufficient to mask the taste of the histamine $H_2$-receptor antagonist, but which allows substantially immediate release of the histamine $H_2$-receptor antagonist after the dosage form is chewed and swallowed, the polymeric coating consisting essentially of a methacrylate ester copolymer which is water-insoluble and water-permeable, and optionally a minor amount of one or more ingredients selected from emulsifiers, wetting agents, drying agents, curing accelerators and stabilizers.

2. The chewable dosage form of claim 1, wherein the methacrylate ester copolymer is a copolymer of ethylacrylate and methylmethacrylate.

3. The chewable dosage form of claim 1, wherein the methacrylate ester copolymer is a copolymer comprising three or more different monomeric units including methylmethacrylate, ethylacrylate, and an aminoalkylmethacrylate.

4. A chewable dosage comprising:
    a histamine $H_2$-receptor antagonist in an amount which is effective to treat a gastrointestinal disorder, the histamine $H_2$-receptor antagonist being selected from the group consisting of ranitidine, anitidine, nizatidine, famotidine, sufotidine, roxatidine, bisfentidine, tiotidine, lamtidine, niperotidine, mifentidine, zaltidine and loxtidine, the histamine $H_2$-receptor antagonist being present in the form of granules which are provided with a polymeric coating, the polymeric coating being present in an amount which is sufficient to mask the taste of the histamine $H_2$-receptor antagonist, but which allows substantially immediate release of the histamine $H_2$-receptor antagonist after the dosage form is chewed and swallowed, the polymeric coating consisting essentially of a water-insoluble and water-permeable methacrylate ester copolymer and optionally a minor amount of one or more ingredients selected from emulsifiers, wetting agents, drying agents, curing accelerators and stabilizers, wherein the methacrylate ester copolymer has the general formula:

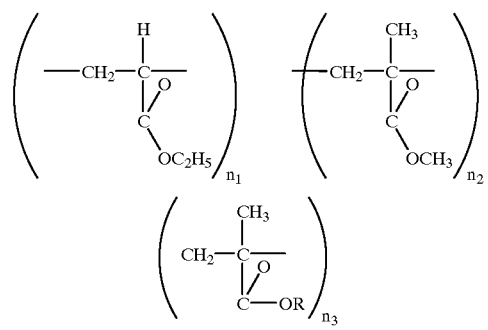

wherein R is an alkyl group having 2 to 12 carbon atoms or an aminoalkyl having from 1 to 12 carbon atoms, and $n_1$, $n_2$ and $n_3$ are selected so that the polymer has a molecular weight of from about 100,000 to about 1,000,000.

5. The chewable dosage form of claim 4, wherein the ratio of $n_1:n_2$ is from about 1:2 to about 2:1, and the ratio of $n_3:(n_1+n_2)$ is at or below about 1:15.

6. The chewable dosage form of claim 5, wherein the methacrylate ester copolymer has a molecular weight of about 800,000.

7. A chewable dosage form comprising:

famotidine in an amount that is effective to treat a gastrointestinal disorder, the famotidine being present in the form of granules that are provided with a polymeric coating, the polymeric coating being present in an amount that is sufficient to mask the taste of the famotidine, but which allows substantially immediate release of the famotidine after the dosage form is chewed and swallowed, the polymeric coating consisting essentially of a methacrylate ester copolymer that is water-insoluble and water-permeable and optionally a minor amount of one or more ingredients selected from emulsifiers, wetting agents, drying agents, curing accelerators and stabilizers, wherein the methacrylate ester copolymer has the general formula:

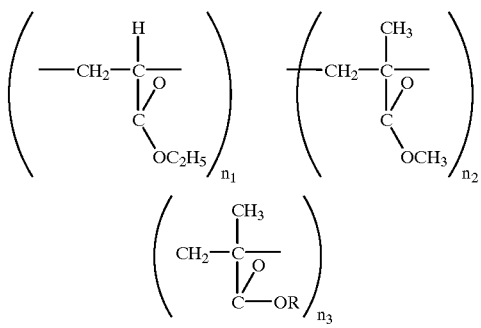

wherein R is an alkyl group having from 2 to 12 carbon atoms or an aminoalkyl having from 1 to 12 carbon atoms, and $n_1$, $n_2$ and $n_3$ are selected so that the polymer has a molecular weight of about 800,000, and wherein the ratio of $n_1:n_2$ is from about 1:2 to about 2:1, and the ratio of $n_3:(n_1+n_2)$ is at or below about 1:15.

8. The chewable dosage form of claim 1, wherein the histamine $H_2$-receptor antagonist is famotidine.

9. The chewable dosage form of claim 1, wherein the histamine $H_2$-receptor antagonist comprises from about 5 to about 50% of the weight of the chewable dosage form.

10. The chewable dosage form of claim 1, wherein the granules containing the histamine $H_2$-receptor antagonist further comprise a binder and a carrier which adds bulk and smoothness to the body of the granules.

11. The chewable dosage form of claim 10, wherein the binder is povidone.

12. The chewable dosage form of claim 10, wherein the carrier is lactose.

13. The chewable dosage form of claim 10, wherein the granules further comprise microcrystalline cellulose.

14. The chewable dosage form of claim 13, wherein the microcrystalline cellulose comprises from about 5% to about 20% of the weight of the granules.

15. The chewable dosage form of claim 10, wherein the histamine $H_2$-receptor antagonist comprises from about 2% to about 85% of the weight of the granules, the binder comprises from about 1% to about 10% of the weight of the granules, and the carrier comprises from about 10% to about 90% of the weight of the granules.

16. The chewable dosage form of claim 1, wherein the coated granules have a size of from about 150 microns to about 2000 microns.

17. The chewable dosage form of claim 16, wherein the polymer coating comprises from about 2% to about 20% of the weight of the coated granules.

18. The chewable dosage form of claim 17, wherein the dosage form is a compressed tablet comprising an extra-granular intense sweetener.

19. The chewable dosage form of claim 18, wherein the intense sweetener is aspartame.

20. A method of forming a chewable dosage form containing a histamine $H_2$-receptor antagonist, comprising:

granulating a mixture comprising a histamine $H_2$-receptor antagonist, a binder, and a carrier to form granules having a size of from about 150 microns to about 400 microns;

applying a polymeric coating to the granules in an amount which is sufficient to mask the taste of the histamine $H_2$-receptor antagonist wherein the dosage form is chewed, but which allows substantially immediate release of the histamine $H_2$-receptor antagonist after the dosage form has been chewed and swallowed, the polymeric coating consisting essentially a methacrylate ester copolymer which is water-insoluble and water-permeable and optionally a minor amount of one or more ingredients selected from emulsifiers, wetting agents, drying agents, curing accelerators and stabilizers; and compressing the polymer coated granules, either alone or with one or more of extra-granular excipients, adjuvants, fillers and/or other active ingredients, to form a chewable tablet.

* * * * *

UNITED STATES PATENT AND TRADEMARK OFFICE
CERTIFICATE OF CORRECTION

PATENT NO. : 6,270,807 B1
DATED : August 7, 2001
INVENTOR(S) : Danielson et al.

It is certified that error appears in the above-identified patent and that said Letters Patent is hereby corrected as shown below:

Column 1,
Line 66, "antagonist" should be -- antagonists --.

Column 2,
Lines 6, 7 and 11, "antagonist" should be -- antagonists --.

Column 3,
Lines 31-45,

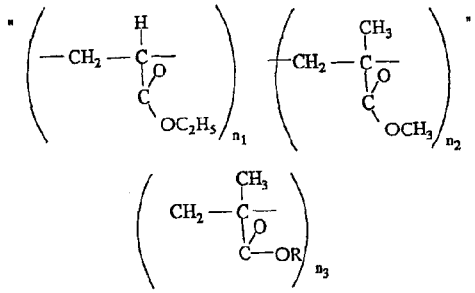

should be

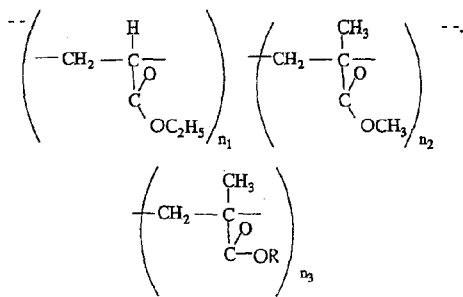

Column 4,
Line 28, "substantial" should be -- substantially --.

Column 5,
Line 30, "may" should be -- made --.

UNITED STATES PATENT AND TRADEMARK OFFICE
CERTIFICATE OF CORRECTION

PATENT NO.    : 6,270,807 B1
DATED         : August 7, 2001
INVENTOR(S)   : Danielson et al.

It is certified that error appears in the above-identified patent and that said Letters Patent is hereby corrected as shown below:

Column 6,
Lines 20-35,

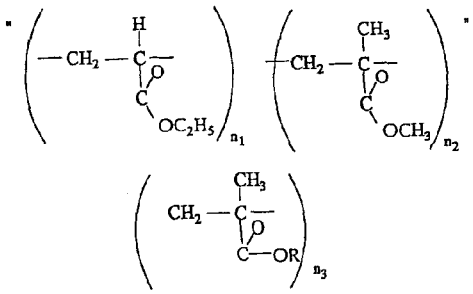

should be

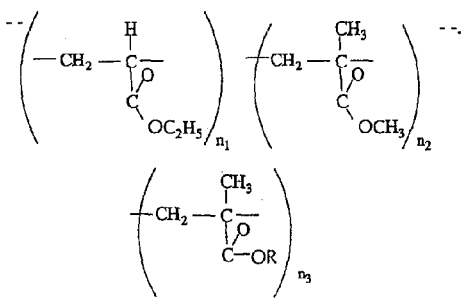

Column 7,
Lines 1-15,

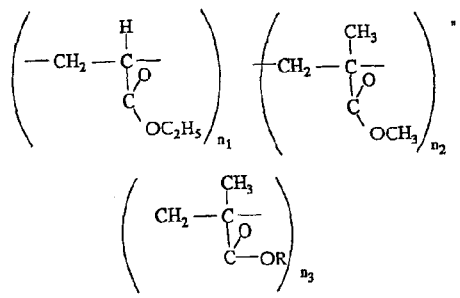

UNITED STATES PATENT AND TRADEMARK OFFICE
CERTIFICATE OF CORRECTION

PATENT NO. : 6,270,807 B1
DATED : August 7, 2001
INVENTOR(S) : Danielson et al.

It is certified that error appears in the above-identified patent and that said Letters Patent is hereby corrected as shown below:

should be

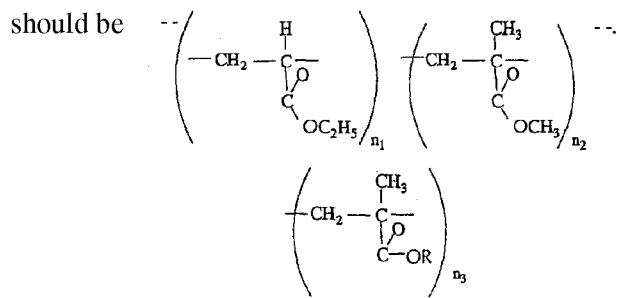

Column 8,
Line 30, after "essentially" insert -- of --.

Signed and Sealed this

Fourth Day of June, 2002

*Attest:*

JAMES E. ROGAN
*Director of the United States Patent and Trademark Office*

*Attesting Officer*